United States Patent [19]

Zaid

[11] Patent Number: 5,089,258

[45] Date of Patent: Feb. 18, 1992

[54] COMPOSITION AND METHOD FOR ABSORBING ODORS USING CITRIC ACID AND CITRATE

[75] Inventor: Najib H. Zaid, Sterling, Kans.

[73] Assignee: Jacam Chemical Partners, Ltd., Sterling, Kans.

[21] Appl. No.: 646,521

[22] Filed: Jan. 28, 1991

Related U.S. Application Data

[63] Continuation-in-part of Ser. No. 594,291, Oct. 9, 1990, abandoned, which is a continuation-in-part of Ser. No. 481,289, Feb. 2, 1990, abandoned.

[51] Int. Cl.$^5$ .................... A61K 31/19; A61K 7/32; A61K 9/14; A61L 9/01
[52] U.S. Cl. .................... 424/76.1; 424/76.5; 424/76.6; 424/65; 424/489
[58] Field of Search ............ 424/76.1, 76.5, 76.6, 424/76.7

[56] References Cited

U.S. PATENT DOCUMENTS

| | | | |
|---|---|---|---|
| 4,690,772 | 9/1987 | Tell et al. | 424/665 |
| 4,839,086 | 6/1989 | Zaid | 252/142 |

*Primary Examiner*—Thurman K. Page
*Assistant Examiner*—E. J. Webman
*Attorney, Agent, or Firm*—Hovey Williams Timmons & Collins

[57] ABSTRACT

Improved odor-reducing compositions, and corresponding methods, are disclosed wherein a substrate or area exhibiting undesirable odors is treated with an odor-reducing composition including respective quantities of citric acid and a salt of citric acid. Preferably, the odor-reducing composition in particulate form includes from about 0.1-20% by weight citric acid, at least about 50% by weight of a salt of citric acid (e.g. sodium citrate) and an anti-caking agent. The compositions of the invention may be used to good effect in the treatment of substrates such as human skin, cloth or other absorbents; or in deodorizing areas exhibiting offensive odors.

11 Claims, No Drawings

COMPOSITION AND METHOD FOR ABSORBING ODORS USING CITRIC ACID AND CITRATE

RELATED APPLICATION

This is a continuation-in-part of Application Ser. No. 07/594,291 filed Oct. 9, 1990, abandoned, which was a continuation-in-part of Application Ser. No. 07/481,289, filed Feb. 2, 1990, abandoned.

BACKGROUND OF THE INVENTION

1. Field of the Invention

The present invention is broadly concerned with compositions and methods for reducing offensive odors on a variety of substrates or in areas exhibiting such odors. More particularly, it is concerned with such compositions and methods wherein use is made of odor-reducing mixtures in both dried, solid, particulate form and in liquid, aqueous dispersion form comprising respective quantities of citric acid and a monovalent salt of citric acid. The compositions of the invention may be used to good effect for reducing or eliminating odors on a variety of substrates, e.g., landfill materials, municipal solid waste, garbage, human skin, cloth, or other absorbents.

2. Description of the Prior Art

It frequently occurs that the skin or clothing of people becomes contaminated with strong or offensive odors. To give but one example, work in and around gasoline stations often results in the strong smell of gasoline on the hands and clothing of workers.

Attempts at using soaps or detergents to remove offensive odors are sometimes effective to a degree, but often the odors persist despite industrious efforts to remove them. It has of course been suggested to employ strong-smelling materials containing perfume or the like to hide or mask offensive odors, but this many times is as disagreeable as the original odors themselves. Accordingly, there is a need for improved odor-reducing compositions which are gentle and easy to use, and which reduce or absorb offensive odors while leaving virtually no residual odors themselves.

Japanese Patent No. 62-139,662 discloses a granular deodorant for use in solid deodorant compositions consisting of 80–90 parts by weight of a ferrous salt, 15–5 parts by weight of citric acid and 5–15 parts by weight of a salt of citric acid. Ferrous salt is the chief constituent of the composition taught by this reference. The citric acid or citrate functions as a stabilizer to prevent oxidation of the ferrous salts. The reference also discloses use of fatty acid salts as a binding agent, but not as a cleansing agent. Moreover, only a solid form of the deodorant is disclosed, and not an aqueous dispersion form. The composition is not formulated to be nontoxic or food grade.

Japanese Patent No. 62-235,364 discloses a deodorant resin composition and articles molded from the resin containing thermoplastic resin and a deodorizing component. A deodorizing component comprised of a 10%–90% zinc compound such as citrate and 90%–10% of an aliphatic polycarboxylic acid such as citric acid is disclosed. In addition, the deodorizing resin composition masks, rather than chemically reacts with aldehydes or other producers of foul odors. This composition is not formulated to serve as a cleaning agent or to function in an aqueous dispersion. The disclosure is limited to use of a divalent zinc compound, which renders it toxic.

Japanese Patent No. 64-8972 teaches an aqueous deodorant dispersion comprised of zinc compounds and aliphatic polycarboxylic acids, such as citric acids, or their salts. The disclosure is limited to zinc compounds. As a consequence, the deodorant compound would be toxic.

Japanese Patent No. 63-161,968 discloses a deodorant composition containing an acidic substance and a ferrate material impregnated with a clay mineral containing polyvalent metal cations. The disclosure is limited to divalent compounds and does not teach a non-toxic compound product. This formulation does not include a cleansing agent or provide for an aqueous dispersion form.

U.S. Pat. No. 3,650,968 discloses a fisherman's soap composition for removing fishy odors. The composition consists of a source of citric acid, a detergent effective in an acid pH range, glycerin, and water. This reference does not teach use of a monovalent salt of citric acid.

U.S. Pat. No. 4,089,942 discloses a cosmetic deodorant composition and process which prevents the formation of odors due to bacterial decomposition of perspiration by maintaining perspiration within a pH range of 3 to 6. The deodorant composition includes a cosmetic carrier, an organic acid such as citric acid, and a salt of an organic acid. Nothing in this reference teaches a composition or method for odor absorption.

U.S. Pat. No. 4,690,772 describes sterilant compositions making use of a water soluble sterilant, a buffer, and a water soluble acid. Among the suggested acids is citric acid, whereas sodium citrate is disclosed as a possible buffering agent. In use, the compositions of this invention are formed as aqueous solutions having a pH of about 7.3, and are very dilute. It is believed that compositions of this character, because of the dilute nature thereof, would be very ineffective as odor reducers; in any event, this utility is nowhere taught or suggested in the '772 Patent.

U.S. Pat. No. 4,839,086 describes compositions useful for the regeneration of cation exchange resins typically found in water softening systems. The compositions described in this patent have been commercialized by JaCam Chemical Co. of Sterling, Kans., and include therein citric acid, a major proportion of a salt of citric acid (sodium citrate), as well as a small quantity of anti-caking agent. The prior art contains no suggestions, however, that compositions of the type described in U.S. Pat. No. 4,839,086, could be useful in the context of odor reduction.

SUMMARY OF THE INVENTION

The present invention overcomes the problems noted above, and provides a greatly improved class of odor-reducing materials. The latter can be formulated and used as dried, particulate compositions, or as relatively concentrated aqueous dispersions. In other instances, the compositions of the invention may be incorporated into a cleansing agent. These broadly types of combined compositions include a cleansing agent (e.g. a soap or detergent) along with an odor-reducing composition mixed with the cleansing agent. The odor-reducing composition includes respective quantities of citric acid and a monovalent salt of citric acid as active ingredients.

The odor-reducing method of the invention involves contracting a substrate exhibiting odors to be reduced with a composition of the type described above, i.e., one including respective quantities of citric acid and a monovalent salt of citric acid. Correspondingly, such a composition may be placed adjacent to an area or zone exhibiting such offensive odors.

The compositions and methods of the invention are usable for absorbing or reducing odors on a wide variety of substrates such as landfills, municipal solid wastes, garbage, human skin, cloth or other absorbents (e.g. litterbox fills); or in open areas such as refrigerators.

DESCRIPTION OF THE PREFERRED EMBODIMENTS

Odor-reducing compositions in accordance with the invention may be fabricated and used in a multitude of forms. For example, the compositions may be in particulate form, and in such instances would include from about 0.1 to 20% by weight citric acid, and at least about 50% by weight of a monovalent salt of citric acid. A salt of any of various monovalent species may be employed, including ammonium and alkali metals such as potassium, sodium, and lithium. In particularly preferred forms sodium or potassium is employed. The resultant product is non-toxic, food-grade, and safe for domestic as well as commercial use. As constituted, the particulate compositions have essentially no odor, but if desired, additives for giving the compositions a pleasant smell may be used. More particularly, such particulate compositions would include from about 0.1–30% by weight citric acid, and from about 70 to 99% by weight of citric acid monovalent salt. Moreover, in order to improve the handling properties of such particulate compositions, they would normally also include a minor amount of an anti-caking agent such as a mixture of mono and dimethyl naphthalene sulfonate sodium salts. A composition of this character is sold by Desoto, Inc. of Des Plaines, Ill. under the designation "Petro AG Special Superfine Powder."

Compositions made in accordance with U.S. Pat. No. 4,839,086 are particularly useful as particulate odor-removing compositions in the invention. Such compositions have heretofore been sold by JaCam Chemical Co. of Sterling, Kans. under the trademark "Ironfite", for use in the regeneration of cation exchange resins. The "Ironfite" product includes about 97.9% sodium citrate, about 2% by weight citric acid, and about 0.1% by weight of the above-described anti-caking agent, and is sold as a particulate powder. Alternately, a mixture of about 80% by weight sodium citrate and 20% by weight citric acid may be used, mixed with a minor amount of anti-caking agent.

If desired, the particulate compositions of the invention may be used directly, or alternately may be incorporated into a cleansing agent. For example, a hand cleanser commercialized under the designation "Gojo" may be used to good effect, with the addition of from about 2–20% by weight of the particulate odor-reducing composition described above mixed therein. More preferably, about 10% by weight of this particulate odor-reducing composition is employed. In such cases, the combined cleanser/odor-reducer may be simply rubbed on to the hands or skin of the user in the normal fashion, and then rinsed off with water. Offensive odors on the skin are virtually completely absorbed or removed by the composition. In other cases a supply of the particulate material may be placed within or in proximity to an area or region exhibiting unpleasant odors.

In other forms of the invention, the citric acid/citric acid monovalent salt materials may be dispersed in an aqueous medium such as water. Here again, use of such an aqueous dispersion would involve contacting the dispersion with a substrate to be treated, followed by rinsing; or placing a container of the liquid in an area to be deodorized. Preferably, the liquid forms of the present invention would include therein at least about 1.5% by weight citric acid, and at least about 15% by weight of a monovalent salt of citric acid; more preferably, the compositions would include in excess of about 2% by weight citric acid, and in excess of about 25% by weight of the salt. In actual practice, liquid compositions have been formulated having 2.2% by weight citric acid, 42.2% by weight sodium citrate with the balance being water. Such liquid compositions can be conveniently used by spraying or dripping them onto an area or substrate to be deodorized. Moreover, these compositions, as well as the corresponding particulate forms, can be readily handled and do not harm human skin.

Where the particulate compositions in accordance with the invention are used directly or incorporated into a cleansing agent, it is advantageous that the particle size of the particulate ingredients be relatively small, and preferably between about 50 and 100 standard mesh size. Also, it is preferred to apply the dried, particulate compositions onto substrates that are either inherently moist or premoistened prior to application of the particulate compositions; this enhances the desired deodorizing action.

U.S. Pat. No. 4,839,086 is hereby incorporated by reference herein.

I claim:

1. A method of reducing odors from a substrate or region exhibiting such odors, said method comprising the steps of providing an odor-reducing composition in particulate form and consisting essentially of from about 0.1 to 30% by weight citric acid and at least about 50% by weight of a monovalent salt of citric acid, and contacting said particulate composition with said substrate or region for odor reduction.

2. The method of claim 1, said salt of citric acid being present at a level of from about 70 to 99% by weight, and from about 1 to 20% of said citric acid.

3. The method of claim 1, said composition including an amount of anti-caking agent therein effective for preventing caking of said composition, said agent comprising a mixture of mono and dimethyl naphthalene sulfonate sodium salts.

4. The method of claim 1, said salt of citric acid being selected from the group consisting of the alkali metal and ammonium salts.

5. The method of claim 1, said method comprising contacting the composition with a substrate taken from the group consisting of landfill, human skin, and cloth.

6. The method of claim 1, wherein said composition is mixed with a cleansing agent, and said cleansing agent is contacted with said substrate.

7. A method of reducing odors from a substrate or region exhibiting such odors, said method comprising the steps of providing an odor-reducing composition in the form of an aqueous dispersion and having therein at least about 1.5% by weight citric acid and at least about 15% by weight of a monovalent salt of citric acid therein, and contacting said aqueous composition with said substrate or region for odor reduction.

8. The method of claim 7, said citric acid being present in excess of about 2% by weight in said composition.

9. The method of claim 7, said salt being present in excess of about 25% by weight in said composition.

10. The method of claim 7, said salt of citric acid being selected from the group consisting of the alkali metal and ammonium salts.

11. The method of claim 7, said substrate being selected from the group consisting of landfill, human skin and cloth.

* * * * *